United States Patent [19]

Srivastava et al.

[11] Patent Number: 4,500,508

[45] Date of Patent: Feb. 19, 1985

[54] RADIONUCLIDE LABELED LYMPHOCYTES FOR THERAPEUTIC USE

[75] Inventors: Suresh C. Srivastava, Setauket; Rashid A. Fawwaz, Pelham; Powell Richards, Bayport, all of N.Y.

[73] Assignee: The United States of America as represented by the United States Department of Energy, Washington, D.C.

[21] Appl. No.: 491,132

[22] Filed: May 3, 1983

[51] Int. Cl.³ .................... A61K 49/00; A61K 43/00
[52] U.S. Cl. ........................................ 424/1.1; 424/9
[58] Field of Search ..................... 424/1.1, 9

[56] References Cited

PUBLICATIONS

Tharur et al., Radiology, 119 (1976) 731–732.
Fawwaz et al., J. Nucl. Med., 23 (1982) p. 58.
Srivastava et al., 4th Int. Symposium on Radio-Pharmaceutical Chemistry, Tulich, W. Germany, Aug. 23–27, 1982, pp. 122–123.
Hardy et al., Surgery, vol. 86 (1979) pp. 194–202.
Van Rooijen, J. Immunological Methods 15 (1977) pp. 267–277.

*Primary Examiner*—Christine M. Nucker
*Attorney, Agent, or Firm*—Margaret C. Bogosian; James W. Weinberger

[57] ABSTRACT

Lymphocytes labelled with $\beta$-emitting radionuclides are therapeutically useful, particularly for lymphoid ablation. They are prepared by incubation of the lymphocytes with the selected radionuclide-oxine complex.

21 Claims, No Drawings

RADIONUCLIDE LABELED LYMPHOCYTES FOR THERAPEUTIC USE

The United States Government has rights to this invention pursuant to Contract No. DE-AC02-76-CH00016, between the U.S. Dept. of Energy and Associated Universities, Inc.

BACKGROUND OF THE INVENTION

It is known that radiosensitive lymphocytes which arise in the reticular tissue of the lymph glands are the cells primarily responsible for the recognition and destruction of allografts. It follows, therefore, that lymphoid ablation should inhibit or prevent the rejection of allografts.

In the past total body irradiation (TBI) utilizing an external beam has been utilized to abrogate allograft rejection. However, the dose of TBI required for a permanent acceptance of an allograft is lethal to bone marrow cells, both proximal and distal, and to the cells of the gastro-intestinal mucosa. This and other complications have led the art to seek immunosuppresive methods employing radioactive compounds, the $\beta$-emissions of which will selectively destroy lymphoid tissue.

It is known that $^{109}$Pd labeled hematoporphyrin, a $\beta$-emitting radioactive agent with a half life of 13.4 hours, a beta emission of 1.028 MeV maximum, and a scatter area of 2 mm can satisfy many of the criteria for this purpose. (Fawwaz et al, J. Nucl. Med. 12:231–236, 1981 and Fawwaz et al, J. Nucl. Med. 15:997–1002, 1974) Palladium-109-hematoporphyrin (Pd-H) preferentially localizes in lymphoid organs as well as in the liver, kidney and central bone marrow. The affinity of Pd-H for distal bone marrow and intestinal tissue is low. In the rat a single treatment of a future transplant recipient with sublethal Pd-H (24 m Ci/Kg) and rabbit anti-rat lymphocyte globulin (ALG) leads to permanent cardiac allograft acceptance across a minor histocompatibility barrier and a significant prolongation across a major histocompatibility difference.

Unfortunately, Pd-H has a relatively high concentration in non-lymphoid organs such as the liver, kidney, adrenals and ovaries. For this reason the art has continued to seek other $\beta$-emitters which will concentrate more selectively in the lymphoid organs, thereby to inhibit the rejection of allografts by lymphoid ablation.

BRIEF SUMMARY OF THE INVENTION

It has been discovered that lymphocytes labeled with a sufficient amount of $\beta$-emitting radionuclide can be prepared, and that these novel products are therapeutically useful for a number of purposes including the treatment of lymphomas, autoimmune diseases and splenic disorders, and to prevent the rejection of allografts.

For these purposes, the mammalian subject in need of such therapeutic treatment may be treated parenterally with the labeled lymphocyte carrying a sufficient amount of $\beta$-emitting radionuclide to be effective for the intended purpose. While an effective dose will vary appreciably with the treated subject, the therapeutic effect to be achieved and other factors known and recognized by skilled physicians and veterinarians, it is generally effective to administer sufficient labeled lymphocytes to amount to 6 to 10 m Ci/kg of body weight. An appropriate dosage level for $^{109}$Pd labeled lymphocytes in dosage forms would be a level sufficient to provide about 40 to 60 u Ci/$10^8$ cells.

Those skilled in this art will recognize that for the preparation of useful dosage forms it is necessary to strike a balance between the amount of radionuclide which is effective to achieve the desired purpose and the amount that a labeled cell can carry without being damaged or killed. The amounts described in the foregoing paragraphs are generally useful for $^{109}$Pd. They may vary with other $\beta$-emitting radionuclides such as $^{67}$Cu, $^{66}$Ni, $^{55}$Co, $^{69}$Zn and $^{90}$Y, all of which are within the purview of this invention. For many purposes $^{109}$Pd is preferred as a radionuclide because of its favorable half life and favorable beta energy. However, it emits a number of cell damaging Auger and conversion electrons. Therefore, beta-emitting radionuclides such as those mentioned above may be preferred in many instances.

It will be recognized that labeled syngeneic and allogeneic cells will be employed for most purposes. However, the invention is also applicable to xenografts.

The efficacy of the labeled lymphocytes of this invention may be enhanced by the coadministration of anti-lymphocyte globulin. For example, to assist in achieving permanency of an allograft in a human, rabbit anti-human lymphocyte globulin may be employed. To treat an auto-immune disease of a bovine, rabbit anti-bovine lymphocyte globulin may be employed. For convenience, all of these globulins are referred to herein as anti-lymphocyte globulins.

The products of this invention are prepared by first forming a radionuclide complex with 8-hydroxyquinoline (oxine) and then incubating the complex with lymphocytes. The process has been described by Thakur et al, Radiology 119: 731–732, 1976 for the preparation of $^{111}$In labeled lymphocytes. This product is not a beta-emitter and is not useful for the purposes of this invention.

To prepare the oxine complex a $^{109}$Pd salt prepared by neutron bombardment of a $^{108}$Pd salt is reacted with oxine in an aqueous buffered medium at an acid pH.

The oxine complex can be used to label the lymphocytes by addition to an aqueous cell suspension at physiological pH followed by incubation for 0.5 to 1 hour at ambient temperature. The resultant product is a mixture containing $^{109}$Pd labeled lymphocytes and free $^{109}$Pd activity. The unbound or free $^{109}$Pd is then removed, preferably with centrifugation, after which the labeled cells can be resuspended and injected.

DETAILED DESCRIPTION OF THE INVENTION

For convenience this invention will be described specifically by reference to $^{109}$Pd labeled lymphocytes and their utility in rats. However, the techniques described are also applicable to other radionuclides and other mammals including humans.

For these studies inbred Lewis (Rt-$1^l$) and ACI (RT-$1^a$) rats were obtained from Microbiological Associates, Walkersville, Md. Hematoporphyrin was purchased from K & K Laboratories of Plainview, N.Y. $^{109}$Pd Cl$_2$/2H$_2$O was prepared in the High Flux Beam Reactor at Brookhaven National Laboratory, Upton, N.Y. Rabbit anti-rat lymphocyte globulin (ALG) was purchased from Microbiological Associates.

$^{109}$Pd-hematoporphyrin was prepared by the method of Doi et al, Int. J. Appl. Radiat. Isotop. 32:877–880, 1981. Briefly, $^{109}$Pd Cl$_2$.2H$_2$O was dissolved in dimethyl sulfoxide (DMSO) with warming and a 20% stoichiometric excess of the N-methylhematoporphyrin (dissolved in water or an acetate buffer) was added. The color immediately changed from brown to pinkish-red indicating the formation of the $^{109}$Pd complex. The solution was stirred at about 150° C. and the DMSO and water were removed under partial vacuum. The residue was then dissolved in 0.05N NaOH and filtered through a 0.45 um syringe-mounted filter.

To prepare $^{109}$Pd oxine complex, enriched $^{108}$Pd Cl$_2$.2H$_2$O(2.03 mg) was neutron bombarded in a sealed quartz ampule for 16 hours using the Brookhaven High Flux Reactor ($5.5 \times 10^{19}$ n s$^{-1}$cm$^{-2}$) to produce 1.82 Ci of $^{109}$Pd. The material was dissolved in 1.6 ml DMSO with gentle heating and stirring. An aliquot of this solution containing 45 mCi of $^{109}$Pd was tranferred into a 30 ml multi-injection bottle containing 5 ml of a 0.1 m acetate buffer, pH 3.5 to 4.0. Next 34 ug of oxine was dissolved in the same buffer to give a molar ratio of oxine to palladium of 2.6. The solution was stirred for from 5 to 30 minutes and the complex extracted with 5 ml chloroform by vortex mixing (90% extraction). The chloroform layer was separated and the solvent evaporated under a N$_2$ stream. The residue was dissolved in 3.0 ml warm absolute ethanol and filtered through a 0.45 um nylon 66 filter.

To label the lymphocytes with $^{109}$Pd-oxine, they were isolated from the lymph nodes of normal Lewis rats. The lymph nodes were minced, pressed through a 60-gauge stainless steel screen mesh, and passed through fine cotton gauze as previously described by Satake et al, Cardiac Transplantation 1:208–216, 1982. The cells were washed twice with medium 199 and suspended in 1 ml phosphate buffered saline (PBS), pH 7.4. Lymphocyte labeling was carried out according to the method of Thakur et al, Radiology 119:731–732, 1976. The $^{109}$Pd oxine was added dropwise to the cell suspension and incubated for 30 minutes. The cells were washed once with medium 199 and resuspended in 1 ml of medium 199. The labeling efficiency varied between 40% and 65%. The lymphocyte viability as determined by trypan blue dye exclusion was 95%.

In a heart transplantation study, adult Lewis rats served as recipients of heterotopic abdominal cardiac allografts from ACI rats. The donor and recipient rats were anesthetized with ether and intraperitoneal chloral hydrate. Transplantation was performed using the technique of Ono et al, J. Thorac. Cardiovasc. Surg. 57:225,229, 1969. The donor aorta and pulmonary artery were anastomosed end-to-side to the recipient's abdominal aorta and inferior vena cava, respectively. The technical failure rate was less than 5 percent. Cardiac allograft survival was assessed by daily abdominal palpation and rejection was considered complete upon cessation of palpable cardiac beat.

In one test designed to determine the efficacy of the valuable products of this invention, Lewis rats (n=12) were infused with $3 \times 10^9$ syngeneic or allogeneic (ACI) $^{109}$Pd oxine labeled lymphocytes. The final concentration of $^{109}$Pd per $10^8$ lymphocytes was 50 uCi $^{109}$Pd and 0.12 mg of carrier Pd. Table 1 shows that i.v. injected $^{109}$Pd oxine labeled lymphocytes did localize in lymphoid tissues and that biodistribution pattern of i.v. injected syngeneic lymphocytes did not differ significantly from that observed following the i.v. injection of allogeneic lymphocytes. At 3 hours post-injection, the spleen, a lymphoid tissue, accumulated 35% to 43% of the injected dose and the lymph nodes accumulated 5% to 8% of the injected dose. The ratio of concentration of radioactivity in the spleen relative to bone marrow and intestinal mucosa was 20:1 and 68:1, respectively; the ratio of concentration of radioactivity in the lymph nodes relative to these organs was approximately 3:1 and 11:1, respectively. At 18 hours, there was no further change in these ratios, indicating the absence of recirculation of $^{109}$Pd labeled lymphocytes from non-lymphoid to lymphoid organs. This suggests that these lymphocytes had been injured, since injured cells concentrate in the spleen, despite the fact that a viability test using dye exclusion performed on these $^{109}$Pd labeled lymphocytes immediately prior to parenteral administration revealed 95% viability. They are, however, clearly useful for lymphoid ablation.

TABLE 1

Distribution Patterns of $^{109}$Pd Oxine Labeled Syngeneic and Allogeneic (ACI) Lymphocytes in Lewis Rats*

| | Syngeneic Cells | | Allogeneic Cells | |
|---|---|---|---|---|
| | 3 Hr | 18 Hr | 3 Hr | 18 Hr |
| Blood | 2.4 ± 0.14 | 0.9 ± 0.02 | 2.5 ± 0.07 | 0.3 ± 0.01 |
| Spleen | 34.8 ± 3.33 | 36.1 ± 1.07 | 41.4 ± 1.58 | 43.2 ± 2.16 |
| Liver | 4.3 ± 0.25 | 5.0 ± 0.16 | 5.6 ± 0.30 | 3.2 ± 0.11 |
| Kidney | 2.3 ± 0.08 | 1.8 ± 0.21 | 2.7 ± 0.22 | 1.6 ± 0.04 |
| Lung | 3.4 ± 0.18 | 0.7 ± 0.02 | 2.3 ± 0.10 | 1.3 ± 0.07 |
| Lymph Node | 5.6 ± 0.19 | 5.3 ± 0.44 | 8.3 ± 0.55 | 7.7 ± 0.62 |
| Bone Marrow | 1.7 ± 0.14 | 1.4 ± 0.1 | 1.9 ± 0.08 | 1.2 ± 0.03 |
| Duodenum | 0.5 ± 0.02 | 0.4 ± 0.04 | 0.4 ± 0.02 | 0.2 ± 0.01 |
| Ovary | 0.2 ± 0.06 | 0.2 ± 0.04 | 0.3 ± 0.07 | 0.3 ± 0.06 |

*50 uCi $^{109}$Pd and 0.12 ug Pd per $10^8$ lymphocytes.
Each animal was infused with $3 \times 10^9$ $^{109}$Pd labeled lymphocytes.
Values represent mean of three animals per data point.

The following experiment illustrates lymph node accumulation as a function of $^{109}$Pd radionuclide and $^{108}$Pd carrier dose. Normal Lewis rats were infused with $10^8$ syngeneic lymphocytes labeled with 0.6 uCi of $^{109}$Pd-oxine while varying the amount of $^{108}$Pd carrier from 0.12 ug to 0.34 ug per $10^8$ cells. Three animals from each of four subgroups were sacrificed for determination of injected dose per gram (ID/g) of lymph nodes at three hours post injection. There was a sharp fall (P<0.001) in accumulation of labeled lymphocytes in lymph node where the Pd carrier was increased from 0.12 ug to 0.34 ug per $10^8$ cells while the radioactivity was kept constant at about 0.6 uCi per $10^8$ cells. A smaller but statistically significant decline (P<0.01) in the accumulation of labeled lymphocytes in lymph nodes occurred when the Pd carrier dose was increased from 0.12 ug to 0.20 ug per $10^8$ syngeneic lymphocytes.

A separate group of normal Lewis rats was infused with $10^8$ syngeneic lymphocytes labeled with varying amounts of radioactive $^{109}$Pd oxine (0.6 uCi to 68.9 uCi per $10^8$ cells) while the amount of Pd carrier was kept constant at approximately 0.12 ug per $10^8$ cells. Three animals from each of these four subgroups were sacrificed for determination of percent ID/g lymph node at 3 hours post injection. When the Pd carrier weight was kept constant there was a small but significant fall ($P<0.01$) of lymph node radio activity from a labeling dose of 21.3 uCi to 54.6 uCi/$10^8$ cells (Table 2).

TABLE 3

Cardiac Allograft Survival (ACI to Lewis)

| Group | Treatment | (N) | Survival Time (Days) | $P_1$ | $P_2$ | $P_3$ |
|---|---|---|---|---|---|---|
| 1 | None | 6 | 6.8 ± 0.42 | — | — | — |
| 2 | ALG 5 mg on days −2, −1 | 6 | 14.1 ± 3.46 | 0.001 | — | — |
| 3 | 3 mCi Pd-H day −4 and ALG 5 mg on days −2, −1 | 6 | 14.6 ± 3.02 | 0.001 | NS | — |
| 4 | 3 mCi Pd-L day −4 and ALG 5 mg on days −2, −1 | 4 | 30.5 ± 3.12 | 0.001 | 0.001 | 0.001 |

$P_1$ is significance level of the difference between the experimental group and the control (untreated) recipients (Group 1).
$P_2$ is significance level of the difference between the experimantal group and the ALG treated group (Group 2).
$P_3$ is significance level of the difference between Group 4 ($^{109}$PD labeled lymphocytes and ALG) and Group 3 (Pd-H and ALG).

TABLE 2

Lymph Node Activity at 3 Hours as Function of Pd-Radioactivity and $^{109}$Pd Carrier Weight*

| | μCi In-111 per $10^8$ Lymphocytes | μCi $^{109}$Pd per $10^8$ Lymphocytes | μg $^{108}$Pd $10^8$ Lymphocytes | % administered dose/gm LN |
|---|---|---|---|---|
| Subgroup A | 1 | 0 | 0 | 17.9 ± 1.09 |
| | 0 | 0.6 | 0.12 | 13.1 ± 0.68 |
| | 0 | 0.6 | 0.16 | 12.0 ± 0.88 |
| | 0 | 0.6 | 0.20 | 7.2 ± 0.034 |
| | 0 | 0.6 | 0.34 | 0.4 ± 0.04 |
| Subgroup B | 0 | 21.3 | 0.12 | 12.7 ± 0.67 |
| | 0 | 41.4 | 0.12 | 11.9 ± 0.50 |
| | 0 | 54.6 | 0.12 | 7.6 ± 0.37 |
| | 0 | 68.9 | 0.12 | 7.5 ± 0.68 |

*% ID/gm of LN ± 1 SD
Three animals per data point

The following experiment shows the effect of $^{109}$Pd labeled lymphocytes in cardiac allograft survival.

Four groups of Lewis rats each were treated in the following manner: Group I received no treatment; Group II was treated with 5 mg of rabbit anti-rat lymphocyte globulin (ALG) on days −2 and −1 prior to cardiac allografting; Group III received 6 mCi/kg $^{109}$Pd labeled hematoporphyrin on day −4 and 5 mg ALG on days −2 and −1 prior to grafting; Group IV was treated with $^{109}$Pd oxine labeled lymphocytes ($2.5 \times 10^9$) carrying 6 mCi/kg of $^{109}$Pd on day −4 then 5 mg of ALG on days −2 and −1 prior to grafting. The results are summarized in Table 3. The mean survival of ACI heart allografts in control Lewis rats was 6.8±0.42 days. Pretransplant treatment of the recipient with 5 mg ALG alone led to a moderate prolongation of ACI cardiac allografts. The treatment of the recipient with 6 mCi of $^{109}$Pd hematoporphyrin per kilogram and two doses of ALG showed no improvement in results obtained with ALG alone. However, when the same dose of ALG was administered to the recipients coupled with $^{109}$Pd labeled lymphocyte pretreatment, cardiac allograft survival was doubled (from 14.1±3.46 days to 30.5±3.12 days; P 0.001).

The foregoing experiments clearly establish the efficacy of radionuclide labeled lymphocytes as carriers to concentrate β-emitters in lymphoid tissue, particularly in the spleen and lymph nodes. It is of special interest to note the high ratio of radioactivity in these organs relative to bone marrow and intestinal mucosa.

The ratios of radioactivity present in spleen relative to bone marrow and intestinal mucosa were 12:1 and 30:1 respectively. The same ratios for lymph node to bone marrow and intestinal mucosa were 4:1 and 8:1. The radioactive dose in bone marrow only 200 rads, and in the intestinal mucosa 50 rads. The gonadal dose (50 rads) is comparable to that obtained following administration of therapeutic doses of $^{131}$I to patients with thyroid cancer.

It thus appears that lymphoid ablation can be effected with minimum risk to bone marrow or intestinal mucosa. This is a distinct advantage for the products of this invention compared to the TBI.

The practical effect of this finding will be understood from an analysis of the results reported in Table 3. The prolongation of survival time with the product of the invention administered in association with ALG is almost twice that achieved with the same dosage of PD-H with ALG.

It is anticipated that the products of this invention will be prepared at or near the place of use just prior to use to utilize the maximum amount of radioactivity.

Medium 199 is a standard nutrient medium available from Gibco. It contains sources of carbohydrate and protein as well as vitamins and trace minerals. It is one of several nutrient media which can be used in this invention, the only proviso being that the constituents must be chemically inert with respect to the selected radionuclide so as not to interfere with the lymphocyte labeling reaction.

What is claimed is:

1. Lymphocytes labeled with a therapeutically effective amount of a $\beta$-emitting radionuclide selected from the group consisting of $^{109}$Pd, $^{67}$Cu, $^{66}$Ni, $^{55}$Co, $^{69}$Zn and $^{90}$Y.

2. A labeled lymphocyte as in claim 1 wherein the label is $^{109}$Pd.

3. A labeled lymphocyte as in claim 1 wherein the label is $^{67}$Cu.

4. A labeled lymphocyte as in claim 1 wherein the label is $^{66}$Ni.

5. A labeled lymphocyte as in claim 1 wherein the label is $^{55}$Co.

6. A labeled lymphocyte as in claim 1 wherein the label is $^{69}$Zn.

7. A labeled lymphocyte as in claim 1 wherein the label is $^{90}$Y.

8. A method of effecting lymphoid ablation in order to prevent the rejection of allografts which comprises parenteral administration of a therapeutically effective amount of syngeneic or allogeneic lymphocytes labeled with a $\beta$-emitting radionuclide selected from the group consisting of $^{109}$Pd, $^{67}$Cu, $^{66}$Ni, $^{55}$Co, $^{69}$Zn and $^{90}$Y.

9. A method as in claim 8 wherein the label is $^{109}$Pd.

10. A method as in claim 8 wherein the label is $^{67}$Cu.

11. A method as in claim 8 wherein the label is $^{66}$Ni.

12. A method as in claim 8 wherein the label is $^{55}$Co.

13. A method as in claim 8 wherein the label is $^{69}$Zn.

14. A method as in claim 8 wherein the label is $^{90}$Y.

15. A method of effecting lymphoid ablation in order to prevent the rejection of allografts which comprises parenteral administration of a therapeutically effective amount of syngeneic or allogeneic lymphocytes labeled with a $\beta$-emitting radionuclide selected from the group consisting of $^{109}$Pd, $^{67}$Cu, $^{66}$Ni, $^{55}$Co, $^{69}$Zn and $^{90}$Y together with anti-lymphocyte globulin.

16. A method as in claim 15 wherein the label is $^{109}$Pd.

17. A method as in claim 15 wherein the label is $^{67}$Cu.

18. A method as in claim 15 wherein the label is $^{66}$Ni.

19. A method as in claim 15 wherein the label is $^{55}$Co.

20. A method as in claim 15 wherein the label is $^{69}$Zn.

21. A method as in claim 15 wherein the label is $^{90}$Y.

* * * * *